(12) United States Patent
Mian

(10) Patent No.: US 11,229,417 B2
(45) Date of Patent: Jan. 25, 2022

(54) NON-VISIBLE RADIATION MEDICAL IMAGING

(71) Applicant: Noreen F. Mian, Loudonville, NY (US)

(72) Inventor: Noreen F. Mian, Loudonville, NY (US)

( * ) Notice: Subject to any disclaimer, the term of this patent is extended or adjusted under 35 U.S.C. 154(b) by 470 days.

(21) Appl. No.: 16/148,386

(22) Filed: Oct. 1, 2018

(65) Prior Publication Data
US 2019/0105006 A1   Apr. 11, 2019

Related U.S. Application Data

(60) Provisional application No. 62/569,461, filed on Oct. 6, 2017.

(51) Int. Cl.
| | | |
|---|---|---|
| *A61B 6/00* | (2006.01) | |
| *A61B 5/01* | (2006.01) | |
| *A61B 5/00* | (2006.01) | |
| *G06T 5/50* | (2006.01) | |
| *H04N 5/225* | (2006.01) | |
| *H04N 5/232* | (2006.01) | |
| *G06T 5/00* | (2006.01) | |

(52) U.S. Cl.
CPC .......... *A61B 6/5205* (2013.01); *A61B 5/0064* (2013.01); *A61B 5/015* (2013.01); *A61B 6/541* (2013.01); *G06T 5/50* (2013.01); *H04N 5/2258* (2013.01); *H04N 5/23219* (2013.01); *H04N 5/23229* (2013.01); *H04N 5/23293* (2013.01); *A61B 5/0071* (2013.01); *A61B 2560/0252* (2013.01); *G06T 5/00* (2013.01)

(58) Field of Classification Search
CPC ..... A61B 5/015; A61B 5/0064; A61B 5/0071; A61B 6/5205; A61B 6/5247; A61B 6/541; A61B 2560/0252; H04N 5/23293; H04N 5/23219; H04N 5/23229; H04N 5/2258; G06T 5/00; G06T 5/50
See application file for complete search history.

(56) References Cited

U.S. PATENT DOCUMENTS

| | | | |
|---|---|---|---|
| 5,272,340 A | * | 12/1993 | Anbar ........................ G01J 3/32 250/330 |
| 7,536,278 B2 | | 5/2009 | Main et al. |
| 2006/0043296 A1 | * | 3/2006 | Mian ..................... G01J 5/0846 250/330 |
| 2008/0275310 A1 | * | 11/2008 | Kim ..................... A61B 5/4266 600/300 |
| 2009/0018721 A1 | | 1/2009 | Mian et al. |
| 2009/0289187 A1 | | 11/2009 | Mian |
| 2010/0100275 A1 | | 4/2010 | Mian et al. |

(Continued)

*Primary Examiner* — Boniface N Nganga
(74) *Attorney, Agent, or Firm* — LaBatt, LLC

(57) ABSTRACT

A non-visible radiation imaging system is provided in which an image is obtained based on non-visible infrared radiation of a subject. The image can be enhanced to increase its resolution. Additionally, the image can be combined with another image based on visible light for the subject. The system also provides for a step by step procedure which must be following to obtain a non-visible radiation image accurately for medical diagnostics. Further, a non-visible radiation diagnostic examination system and method are provided that perform an automatic diagnostic information extraction based on examination of the subject using one or more of the images.

20 Claims, 9 Drawing Sheets

(56) References Cited

U.S. PATENT DOCUMENTS

2013/0268155 A1    10/2013   Mian et al.
2013/0313433 A1    11/2013   Mian et al.
2014/0136047 A1     5/2014   Mian et al.
2016/0003678 A1     1/2016   Mian et al.

* cited by examiner

NON-VISIBLE RADIATION MEDICAL IMAGING

REFERENCE TO RELATED APPLICATIONS

The current application claims the benefit of U.S. Provisional Application No. 62/569,461, filed on 6 Oct. 2017, which is hereby incorporated by reference.

TECHNICAL FIELD

The disclosure relates generally to imaging and diagnostics, and more particularly, to imaging non-visible (including thermal, near infrared all the way up to infrared) radiation and/or visible light for a subject, and to perform medical imaging and diagnostics of human or animal subjects using the non-visible radiation and/or visible light image(s).

BACKGROUND ART

Numerous imaging devices exist for generating images of human subjects based on electromagnetic radiation in the spectral band. However, additional information on one or more attributes of many subjects can be obtained from imaging electromagnetic radiation having wavelengths that fall above and/or below visible light in the infrared spectral band. For example, infrared light (e.g., thermal radiation) can be imaged to determine the temperature characteristics of the subject. Other radiation spectra having non-visible wavelengths that may provide useful information include ultraviolet light, X-rays, radio waves, and the like.

To date, three major technologies are used to detect and/or measure infrared light. A bolometer, which includes an extremely fine wire in an electrical circuit, can measure temperature based on a change in conductance in the wire. When only a particular spectrum of radiation, such as infrared light, is permitted to reach the bolometer, the radiation can be measured. Similarly, a pyroelectric device can measure radiation by exposing a particular type of crystal to a particular spectrum of radiation. Finally, a thermopile, which includes numerous thermocouple elements, can measure radiation based on temperature changes for each element.

Each technology has been used to create an imaging device for infrared light. In particular, a two-dimensional matrix of a selected detection technology can be combined with proper optics to generate a two-dimensional image of radiation in the infrared spectrum. A similar matrix design is used in modern digital cameras for generating visible light images. However, to date, infrared imaging solutions have lagged in both resolution and cost as compared to visible light imaging solutions. As a result, only small resolution infrared imaging systems that use a thermopile array are available for an affordable price (e.g., less than a few hundred dollars). However, these imaging systems have an insufficient resolution for many demanding medical applications.

To date, numerous solutions have been proposed that seek to obtain additional resolution from low-resolution images, particularly visible light images. These solutions include a one-pass super-resolution solution, a simple cubic or bilinear resampling, and the like. A more complex solution comprises a longer-term super-resolution approach that attempts to extract data through complex averaging methods from multiple low-resolution images.

Additional information on a subject can also be obtained by fusing two or more images. Image fusion combines images from one or more sensing modalities, e.g., infrared light and visible light, into a single presentation that retains the useful and unique information from both modalities. Properly done, an image fusion presentation can be synergistic. That is, the fused presentation allows the viewer to comprehend more of the totality of the subject being imaged. As a result, a need exists for an improved imaging and/or examination solution that can incorporate imaging of non-visible radiation (e.g., infrared light) in a cost-effective manner. In particular, a need exists for an imaging system and an examination system and method that generate and use an image based on non-visible radiation of the subject.

However, users must observe strict regime in order to acquire useful infrared images. Unless a strict process and procedure is followed, the infrared images will not be as useful in medical diagnostics on human beings or other living bodies. Proper environment control temperature, humidity control, emissivity verification, etc. are just some of the steps needed to be observed before a scientifically useful medical thermal image can be obtained.

Also, the infrared images must be processed by using innovative algorithms to enhance them so that most of the information from the infrared images, fused with visible images or as is infrared images, can be clarified, enhanced, or improved to obtain underlying human medical diagnostic information. It should be noted that typical infrared images obtainable from lower cost, affordable imagers are typically noisy and not very clear, which is not suitable or required for medical diagnostics and medical work.

Last but not the least, the medical infrared images must be processed in a systematic way without taking a lot of time from the healthcare provider to allow the provider with an easy and automated means to extract medical diagnostic information. Especially, when a provider with limited time is trying to arrive at a diagnostic conclusion, lots of images must be compared automatically to reduce human error and improve decision time simultaneously.

SUMMARY OF THE INVENTION

The invention provides a non-visible infrared radiation imaging system for medical diagnostic purposes on humans or animals. Specifically, under the present invention, one or more images of a subject can be obtained based on non-visible radiation of the subject. Additionally, one or more visible light images can be obtained for the subject. In the latter case, a subject image can be generated based on the non-visible infrared spectral band radiation image(s) and the visible light image(s). In any event, the non-visible radiation image(s) can have a lower resolution obtainable from an affordable imager that is enhanced to increase the amount of resolution for the radiation image. We discuss many different methods to enhance the images: the visible light image(s) and/or other data on the subject can be used to generate the enhanced image; image enhancement techniques suitable for images enhancement are used; image processing techniques are used to enhance the information of interest, e.g. a human tumor. As a result, a lower resolution and therefore affordable cost, non-visible radiation imaging system can be used to obtain the desired imaging resolution.

The invention also provides a non-visible radiation examination system and method. In particular, one or more of the images discussed above can be used to examine/monitor one or more characteristics of the subject. The images can be presented for review by a healthcare provider and/or analyzed to diagnose health related issues. In either case, the analysis can use subject data that is obtained from the user and/or the processing of one or more of the images. In addition, one or more actions can be automatically performed based on the analysis. As a result, an examination of the subject can be performed that incorporates the use of one or more images based on non-visible radiation.

A first aspect of the invention provides a non-visible radiation imaging system comprising: means for obtaining a radiation image of a subject based on non-visible radiation of the subject; means for generating an enhanced image based on the radiation image, wherein the enhanced image has a higher resolution than the radiation image; and means for processing the radiation image to automatically extract useful diagnostic information; and displaying at least one of the radiation image or the enhanced image.

A second aspect of the invention provides a medical imaging system comprising: means for obtaining an infrared light image of a subject; means for obtaining a visible light image of the subject; means for displaying an enhanced subject image based on at least one of the infrared light image or the visible light image; and means for managing at least one of the infrared light image, the visible light image or the subject image.

A third aspect of the invention provides a non-visible radiation examination system comprising: means for obtaining a radiation image of a subject being inspected based on non-visible radiation of the subject; means for generating an enhanced image based on the radiation image, wherein the enhanced image has a higher resolution and clearer than the original radiation image; and means for determining a medical diagnostic situation based on the radiation image and a set of diagnostic examination parameters.

A fourth aspect of the invention provides a method of automatically creating diagnostic results on a subject, the method comprising: obtaining a radiation image of the subject based on non-visible radiation of the subject; obtaining a visible light image of the subject; generating a subject image based on the radiation image and the visible light image; and performing the diagnostics based on the subject image and a set of examination and diagnostic parameters where automatic diagnostic information extraction process is carried out on the images.

The fifth aspect of this invention provides a set of steps, guidelines and procedures for the users of this invention to follow so that proper non-visible images are obtained. These steps can help to insure high quality and clinically useful images are gathered. The illustrative aspects of the present invention are designed to solve the problems herein described and other problems not discussed, which are discoverable by a skilled artisan.

The sixth aspect of this invention is to use the high resolution visible image to perform image processing thereby generating cues to help automatically locate critical areas and thermal information in the fused image, collocated thermal image, etc. Thermal images are hard to process; however, high resolution visible images are easy to perform automatic image processing to extract regions of interests which can be used to zoom in on critical areas of interest. For example, one can automatically obtain thermal details of subject's ear by using the above method.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, the invention provides a non-visible radiation imaging system for medical diagnostic purposes. Specifically, under the present invention, one or more images of a subject can be obtained based on non-visible radiation of the subject. Additionally, one or more visible light images can be obtained for the subject. In the latter case, a subject image can be generated based on the non-visible radiation image(s) and the visible light image(s): first by fusing the two types of images together and second by using visible image as a template to the non-visible image. In any event, the non-visible radiation image(s) can have a lower resolution, typically 640×480 pixels available commercially at an affordable price, that is enhanced to increase the amount of resolution for the radiation image. The visible light image(s) and/or other data on the subject can be used to generate the enhanced image. As a result, a lower resolution, and therefore lower cost, non-visible radiation imaging system can be used to obtain the desired imaging resolution.

The invention also provides a non-visible radiation diagnostic examination system and method. In particular, one or more of the images discussed above can be used to examine/monitor one or more diagnostic parameters of the subject. The images can be presented for review by a healthcare provider or a user and/or analyzed to determine impending health issues. In either case, the analysis can use subject data that is obtained from the user and/or the processing of one or more of the images. In addition, one or more analyses can be automatically performed based on the innovative algorithms. As a result, a diagnostic examination of the subject can be performed that incorporates the use of one or more images based on non-visible radiation.

Figure 1:
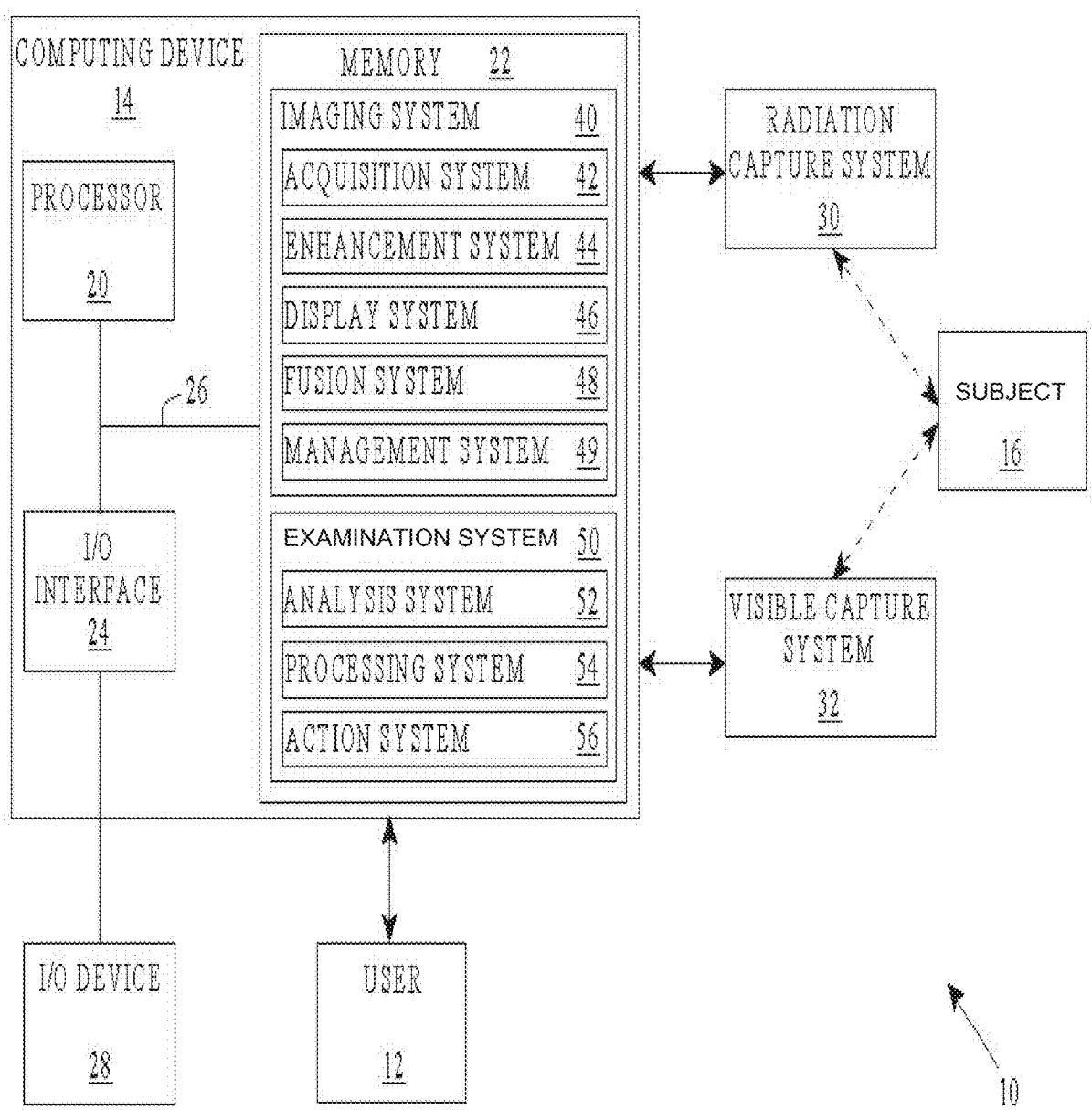
FIG. 1 shows an illustrative system for performing an examination of a human subject.

Turning to the drawings, FIG. 1 shows an illustrative system 10 for performing an examination on a subject 16. As used herein, the subject 16 is used to represent any human being or animal capable of being imaged. To this extent, the subject 16 can comprise a single physical item (e.g., an entire human), a physical item made of a plurality of physical items (e.g., many human body parts), and the like. Further, the subject 16 can comprise an area that may include one or more physical items, such as the perimeter of an abdomen. As a result, the term "subject" does not limit the invention to any particular type of examination and/or imaging application.

The system 10 includes an imaging system 40 that can obtain and manage one or more images of the subject 16 from a radiation capture system 30 and/or a visible capture system 32. The radiation capture system 30 obtains radiation image(s) of the subject 16 based on non-visible radiation of the subject 16. In an embodiment, the non-visible radiation can comprise infrared light (e.g., thermal radiation). However, it is understood that a radiation image can be obtained for other types of non-visible electromagnetic radiation, including ultraviolet light, radio waves, gamma rays, electric waves, microwaves, and the like. The visible capture system 32 obtains visible light image(s) of the subject 16 that are based on electromagnetic radiation having frequencies within the visible light spectrum (i.e., visible light) for the subject 16. To this extent, the visible capture system 32 can comprise any type of visible light sensing device for the imaging subject 16. Typical commercially available visible light sensing devices are 10 mega pixels or higher resolutions and can be affordable.

In any event, an examination system 50 can perform an examination of the subject 16 based on the radiation image(s) and/or visible light image(s). As used herein, the term "examination" means any type of examination/monitoring of the subject 16 that seeks to obtain diagnostic information on the subject 16 for any purpose. For example, an "examination" can comprise an examination of a human patient, or the like; an examination of an animal for overheating due to racing; an examination of a human over time to reveal developing tumors, and the like.

An imaging system 40 and the examination system 50 are each shown as implemented on a computing device 14 as a program product. However, it is understood that some or all of the functionality described for the imaging system 40 and/or the examination system 50 could be implemented as hardware and/or firmware. Regardless, the radiation capture system 30 and/or the visible capture system 32 can comprise one or more digital sensing devices that obtain image(s) in the form of digital data based on the non-visible radiation and/or visible light for the subject 16. In this case, the radiation capture system 30 and/or the visible capture system 32 can provide the image(s) to the imaging system 40 and/or the examination system 50 in a format that can be readily processed by either system. In one embodiment, the radiation capture system 30 and/or the visible capture system 32 can utilize a line/group scanning approach to generate the corresponding image, rather than the typical gestalt approach commonly incorporated in imaging devices.

In any event, the computing device 14 can comprise any type of computing system capable of being operated by a user 12 and/or communicating with one or more other computing systems. In one embodiment, the computing device 14, the radiation capture system 30 and/or the visible capture system 32 are implemented as a unitary handheld imaging system as shown and discussed further below in FIG. 7A. Alternatively, the computing device 14 can comprise a standard computing system such as a desktop/laptop computing system, a personal digital assistant (PDA), a palmtop, a multi-function mobile telephone, etc., that is capable of being programmed with and executing one or more program products, such as the imaging system 40 and/or the examination system 50. In this case, the radiation capture system 30 and/or the visible capture system 32 can be implemented as a separate physical system that communicates with the computing device 14 via a standard communications technology.

To this extent, the computing device 14 is shown including a processor 20, a memory 22, an input/output (I/O) interface 24, a bus 26, and an I/O device 28. In general, processor 20 executes computer program code, such as the imaging system 40, that is stored in memory 22. While executing the computer program code, the processor 20 can read and/or write data (e.g., image(s) of the subject 16) to/from the memory 22 and/or the I/O interface 24. A bus 26 provides a communications link between each of the components in the computing device 14, while the I/O device 28 provides a communications link between the computing device 14 and the user 12, the radiation capture system 30, and/or the visible capture system 32.

The computing device 14 is only illustrative of various possible combinations of hardware. For example, the processor 20 may comprise one or more processing units that share the execution of the imaging system 40 and/or the examination system 50. Similarly, the memory 22 can comprise any combination of various types of read only, read/write, fixed, portable, volatile, nonvolatile, etc., computer-readable mediums and/or devices. Further, the I/O interface 24 can comprise any system for exchanging information with one or more I/O devices 28, which in turn provide an interface (e.g., a communications port, a wireless communications system) with one or more other computing systems and/or an interface (e.g., a pointing device, a display, etc.) with the user 12. It is understood that the radiation capture system 30 and/or the visible capture system 32 can include the same components (e.g., processor, memory, I/O interface, etc.) as shown for the computing device 14. These components have not been separately shown and discussed for brevity.

In any event, the user 12 can utilize the imaging system 40 to obtain and manage radiation and/or visible light image(s) for subject 16. To this extent, the imaging system 40 is shown including an acquisition system 42 for obtaining radiation and/or visible light image(s) of subject 16, an enhancement system 44 for generating an enhanced image of the subject 16 based on the radiation and/or visible light image(s), a display system 46 for displaying an image to the user 12, a fusion system 48 for generating a subject image based on the radiation and visible light image(s), and a management system 49 for managing the various image(s) for the subject 16. Similarly, the user 12 can utilize the examination system 50 to perform an examination of the subject 16 using the radiation and/or visible light image(s). To this extent, the examination system 50 is shown including an analysis system 52 for determining a situation (e.g., a medical condition) based on the radiation image(s), a processing system 54 for generating subject data based on the radiation image(s), and an action system 56 for performing an action in response to the situation.

Operation of each of the systems is discussed further below. However, it is understood that some of the various systems shown in the imaging system 40 and the examination system 50 can be implemented independently, combined, and/or implemented on another computing system. For example, the examination system 50 could be implemented on a separate computing system from the imaging system 40. To this extent, the imaging system 40 could be implemented on the radiation capture system 30 and/or a computing system that includes both the radiation capture system 30 and the visible capture system 32. Additionally, it is understood that some of the systems and/or functionality may be partially implemented, not implemented, or additional systems and/or functionality may be included within the system 10.

Figure 7B:
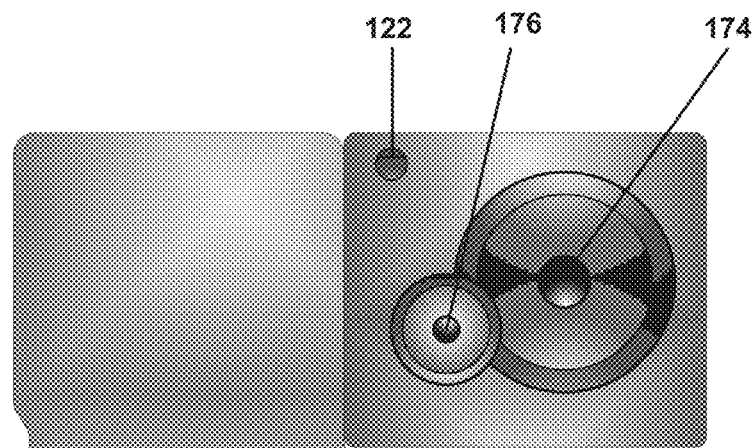
FIGS. 7A-B show alternative views of an illustrative personal digital assistant (PDA) and sensor head according to one embodiment of the invention.
Figure 7A:
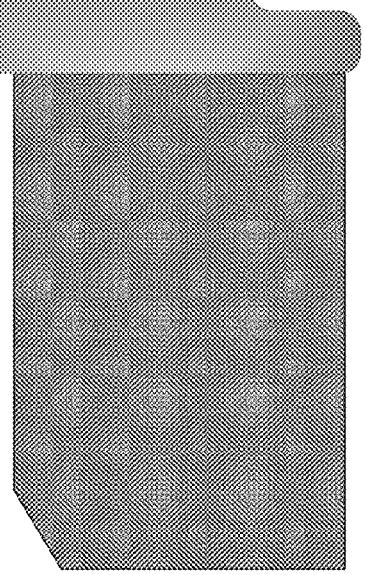
Figure 7A:
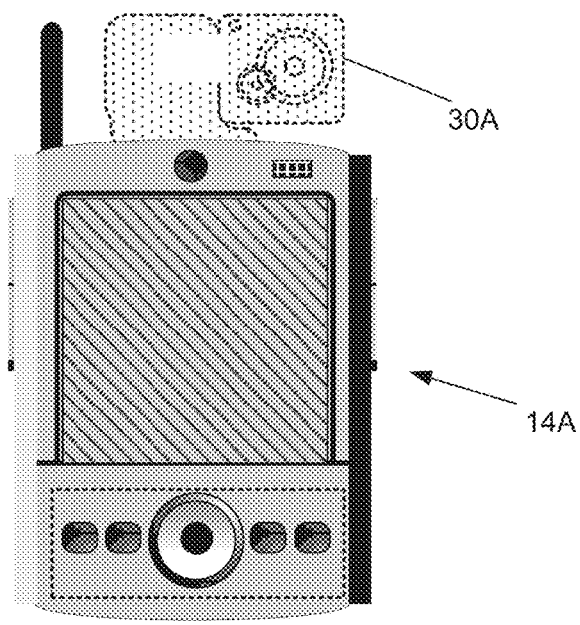

As noted above, one embodiment of the invention provides a non-visible radiation imaging system. To this extent, the radiation capture system 30 can be implemented on a sensor head unit that can be attached to the computing device 14. For example, FIGS. 7A-B show alternative views of an illustrative PDA 14A and the sensor head 30A. As shown in FIGS. 7A-B, the sensor head 30A can mount to the PDA 14A such that it can be operated as a physical extension of the PDA 14A. In an embodiment, the sensor head 30A can include a multi-spectral flash 122, and a pair of imaging devices, such as visible imaging optics 176 and thermal imaging optics 176. In one embodiment, the mounting system can include a connector (male) that can mate with a communications slot (female) included on the PDA 14A to enable communications between the sensor head 30A and one or more systems on the PDA 14A, such as the imaging system 40 (FIG. 1). It is understood that the PDA 14A and the sensor head 30A are only illustrative, and the invention provides various alternative embodiments as will be recognized by one in the art.

Figure 2:
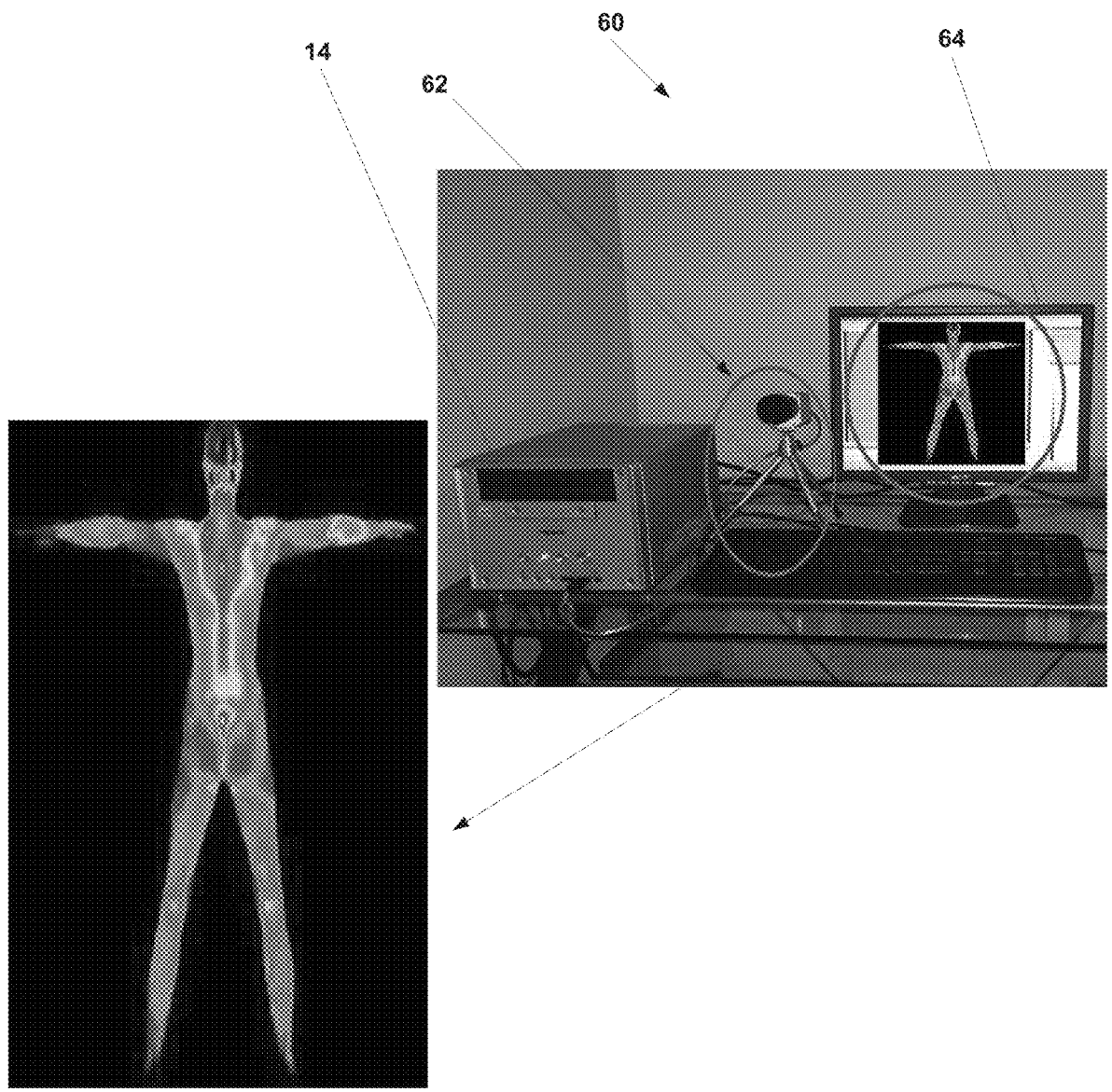
FIG. 2 shows typical human diagnostic setup to be used in a provider's office as a preferred embodiment.

Alternatively, the radiation capture system 30 can be included as part of the computing device 14, which is manufactured as a table top non-visible radiation imaging system. FIG. 2 shows an illustrative tabletop non-visible radiation imaging system 60 ("tabletop system") according to one embodiment of the invention. Various aspects of the invention will be discussed with reference to the tabletop non-visible radiation imaging system 60. However, it is understood that some or all of the functionality could be implemented apart from the tabletop non-visible radiation imaging system 60. In any event, referring to FIGS. 1 and 2, the tabletop non-visible radiation imaging system 60 is shown imaging a person, and can include the various elements shown and described for the computing device 14 together with the radiation capture system 30. Further, the tabletop non-visible radiation imaging system 60 is shown including a combined visible and non-visible camera 62 and a digital display 64 for displaying an image 70. To this extent, the tabletop non-visible radiation imaging system 60 can be operated by a user 12 in a manner similar to digital cameras that are widely known for generating images from visible light and/or non-visible light.

In particular, the user 12 can request, via an I/O device 28 such as a button, that the acquisition system 42 obtain a radiation image. Alternatively, the acquisition system 42 could automatically determine a set of conditions (e.g., a change in temperature, a movement, etc.) that indicate that a radiation image is desired. In either case, the acquisition system 42 can instruct the radiation capture system 30 to generate the radiation image, which in turn can obtain a digital radiation image 72. The radiation capture system 30 can provide the digital radiation image 72, which is shown enlarged adjacent to the tabletop non-visible radiation imaging system 60, to the display system 46 for displaying to the user 12 via the digital display 64. However, it is understood that various alternatives are possible. For example, a display could be included in an eyepiece, the radiation image could comprise an analog image that is subsequently converted to a digital data format, etc.

As noted previously, it can be cost-prohibitive to obtain a raw infrared image having a high resolution. As a result, the tabletop non-visible radiation imaging system 60 can include an enhancement system 44 for generating an enhanced image that has a higher resolution than the raw radiation image 72. The enhancement system 44 can implement one or more of various solutions for generating the enhanced image. For example, one or more of various interpolation/enhancement solutions, such as bilinear and/or Bicubic resampling, can be applied to the radiation image 72 to generate the enhanced image, as is known in the art. Other image enhancement solutions that can be implemented by the enhancement system 44 include noise filtering and reduction, multiple pixel sample averaging, interpolation and super-resolution enhancement through multiple or single image means, image averaging or subtracting, Weiner filters, Kalman filtering of multiple readings, etc. Subsequently, the enhancement system 44 can provide the enhanced image to the display system 46 for display to the user 12.

Figure 4A:
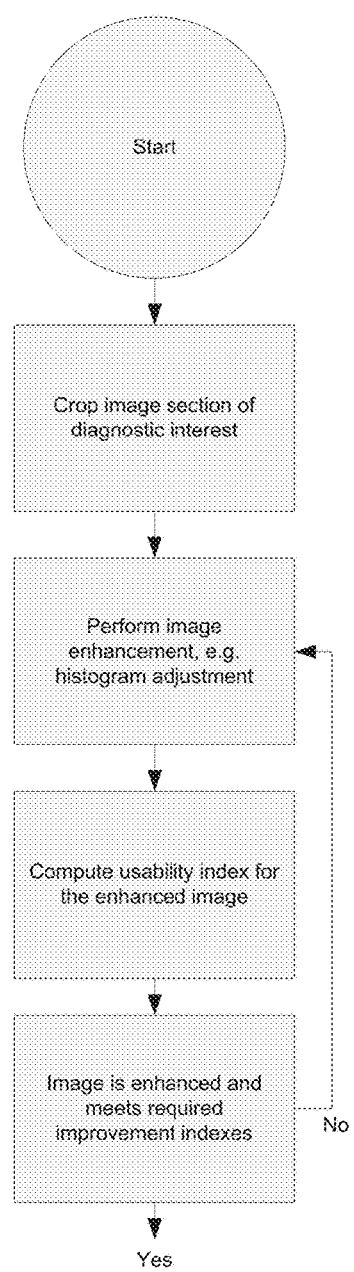
FIG. 4A-C shows illustrative method steps to enhance the images according to one embodiment of the invention.
Figure 4B:
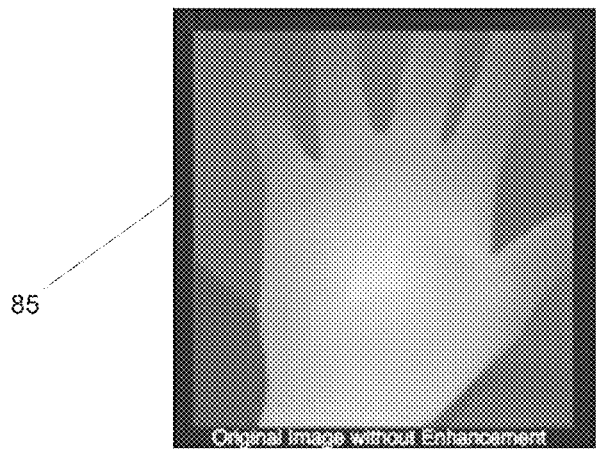
Figure 4C:
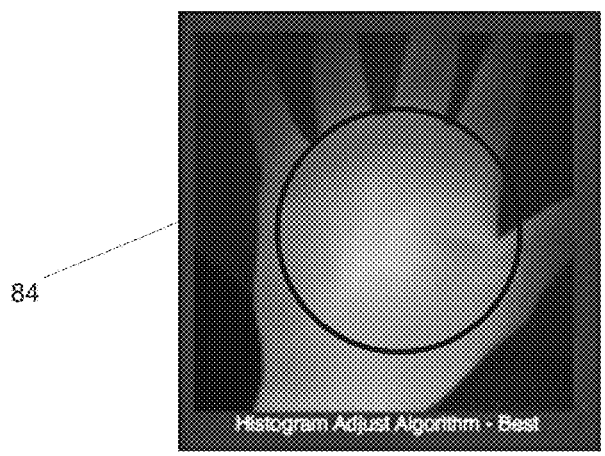

Returning to FIG. 1, the enhancement system 44 can incorporate additional information apart from the radiation image 72 in order to generate the enhanced image 84 (FIG. 4C). For example, the user 12 can provide information on the subject 16 to the acquisition system 42. The information can include, for example, one or more characteristics of the subject 16. Subsequently, the one or more characteristics can be used by the enhancement system 44 to generate the enhanced image of the subject 16. For example, one or more emissivity characteristics of the subject 16 can be considered when generating the enhanced image of the subject 16. To this extent, a subject who is using makeup that has a low emissivity value would appear cooler than a subject such as a person with no makeup, which has a relatively high emissivity value, despite the two subjects being the same temperature. By using the emissivity characteristics of the subject 16, more accurate and detailed information can be derived from an image.

Additionally, one or more characteristics of the subject 16 can be automatically obtained by the acquisition system 42. For example, as mentioned above, the system 10 and/or the tabletop non-visible radiation imaging system 60 can further include a visible capture system 32 for obtaining a visible light image of the subject 16. In one embodiment, the combined visible and non-visible camera 62 (FIG. 2) can include a subjective lens that focuses and allows both visible light and non-visible radiation (e.g., infrared light) to pass through for imaging by the visible capture system 32 and the radiation capture system 30, respectively. To this extent, the acquisition system 42 can request that both of the systems 30, 32 obtain the respective images simultaneously, and both images can comprise substantially similar fields of view. As a result, the visible light image can be readily applied to enhance and interpret the radiation image, and vice versa.

Figure 3:
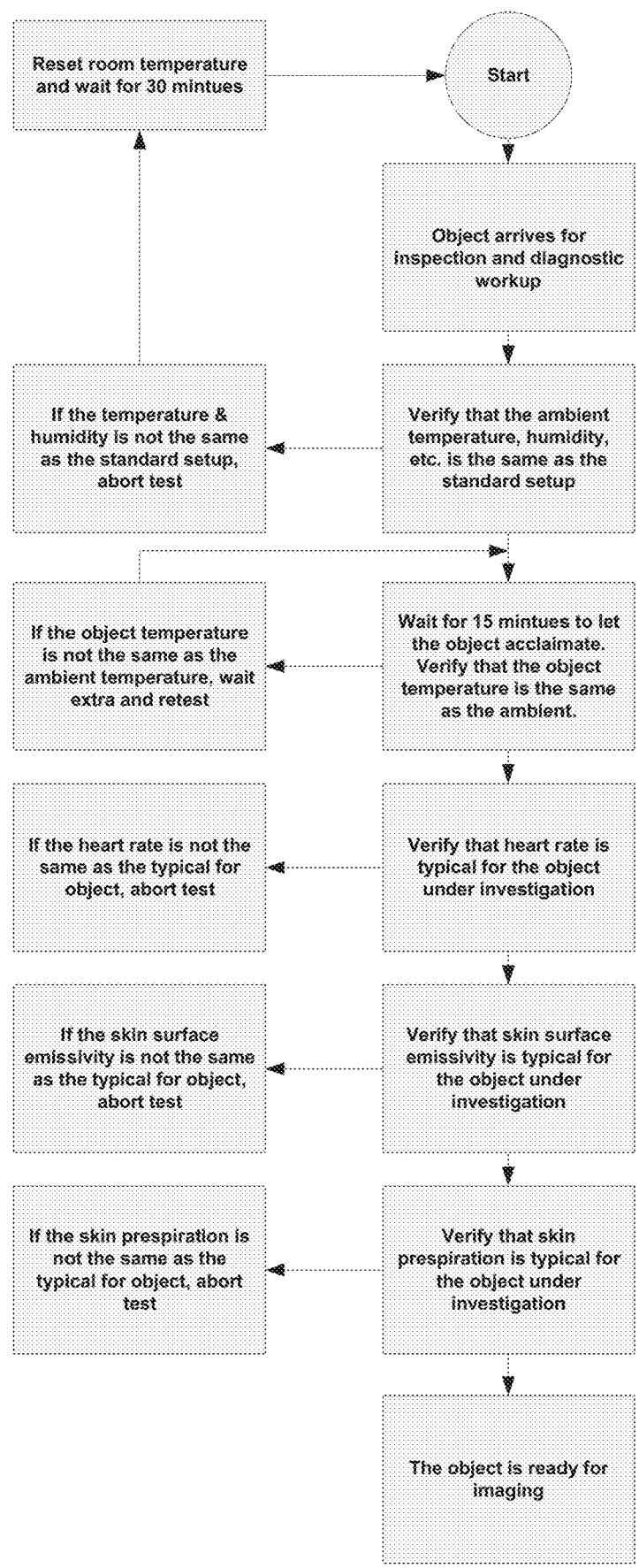
FIG. 3 shows an illustrative process that the user of a radiation imaging system must follow to gather useful images according to one embodiment of the invention.

Turning now to FIG. 3, an illustrative process for determining whether a subject is ready for imaging according to an embodiment is shown. In particular, the process shown in FIG. 3 is directed towards human subjects. While others have tried to develop and use thermal imaging as a non-visible radiation-based system to diagnose human subjects, without implementing the process illustrated in FIG. 3 of the present invention, any diagnostic imaging system will not function to its potential and will have limited diagnostic value. The process shown in the FIG. 3 starts with the human subject arriving for an exam. The first step is to verify if the room is set at the same temperature and humidity level as before. In an embodiment, the temperature and humidity level verifications will be done by a set of sensors included in the acquisition system 42. If the system verifies that the room temperature and humidity levels are consistent and substantially the same as the standardized room temperature and humidity levels, then the process can continue.

Next, the human subject must wait for roughly 15 minutes to get his body acclimated with the room environment. This is essential to make sure that the subject body is roughly at the same temperature to allow thermal imaging system to discern small temperature changes. After roughly 15 minutes, the system automatically acquires a rough complete body image of subject and establishes if the body has reached the room temperature level. If the subject has not reached the room temperature, then the diagnostic work must wait for the subject temperature to come up to the same level. However, if the subject temperature has reached the ambient temperature, then the diagnostic work can continue.

The system can then acquire subject heart rate by using one or more sensors available in the art, e.g. human pulse detectors commonly found in commercial pulse Oximeters. Also, the heart rate can be acquired remotely by using remote heart rate acquisition methods such as microwave based remote hear rate sensors. Next in the process, the system will insure that the subject is not under any duress or emotional stress by measuring respiration rate by using visible imaging to acquire chest movements. Once it is determined that the subject is not under any duress or emotional stress, the system will next verify that the subject skin surface emissivity falls within normal skin emissivity for the same subject by using alternate IR sensors which are spread in the IR spectra. Surface emissivity measurement is necessary to ensure that subject is not using any makeup which can interfere with radiation measurements for the subject. There are commonly available IR sensors which are used to measure a surface emissivity. Next, the skin perspiration is measured by measuring surface reflection by using the visible camera and ordinary visible light. If the subject does not show any particular change in perspiration, then system prompts the provider to take subject/subject image for diagnostic analysis.

Turning now to FIG. 4A, an illustrative process of enhancing a non-visible radiation image according to an embodiment is shown. Present art in the thermal imaging work does not show any image enhancements which would lead to better and improved thermal images. The process of image improvement starts with a thermal image. That is, a non-visible radiation image can be obtained. Next, the system would extract, via cropping, a portion of the non-visible radiation image which is of interest, e.g. the thermal image of a hand shown in FIG. 4B. The cropping function is carried out by using an innovative method which will use the high-resolution visible image as a cue. For example, presently available visible imagers are readily available in 20 mega pixels or even higher resolution. Visible images are easily obtained which can be used for high definition templates or image map to use to dissect and crop regions of interest (ROI) in much lower resolution thermal images.

Note that higher resolution visible images are easily usable by shape recognition algorithms as opposed to lower resolution images. Once the thermal image ROI is cropped, image enhancement is then carried out on the thermal image. In an embodiment, a histogram adjustment of the thermal image shown in FIG. 4B. As can be seen in the enhanced image shown in FIG. 4C, the human hand veins are more easily visible when compared to un-enhanced image shown in FIG. 4B.

As the system performs the image enhancement automatically, the system next computes enhancement quality index by using image quality computations readily known to anyone in the art. If the enhanced image meets the image quality index level, then the enhancement process is stopped. However, if the enhanced image does not meet the image quality index threshold, then the image enhancement is continued by using other image enhancement techniques, e.g. contrast adjustment, speckle removal, Weiner filters, etc. Image averaging is yet another image enhancement technique used to create a better thermal image whereby multiple, i.e. more than one image, is temporarily averaged to reduce pixel noise or image noise thereby creating a better thermal image.

Returning to FIG. 1, the imaging system 40 can include a fusion system 48 for generating a subject image for the subject 16 that is based on non-visible light image 85 (FIG. 4B) and a visible image. To this extent, the fusion system 48 can fuse a visible light image and either the raw radiation image 85 (FIG. 4B) or enhanced image 84 (FIG. 4C) that is generated based on radiation image 85. In any event, the fused image can be provided to the display system 46 for display to the user 12.

Figure 5A:
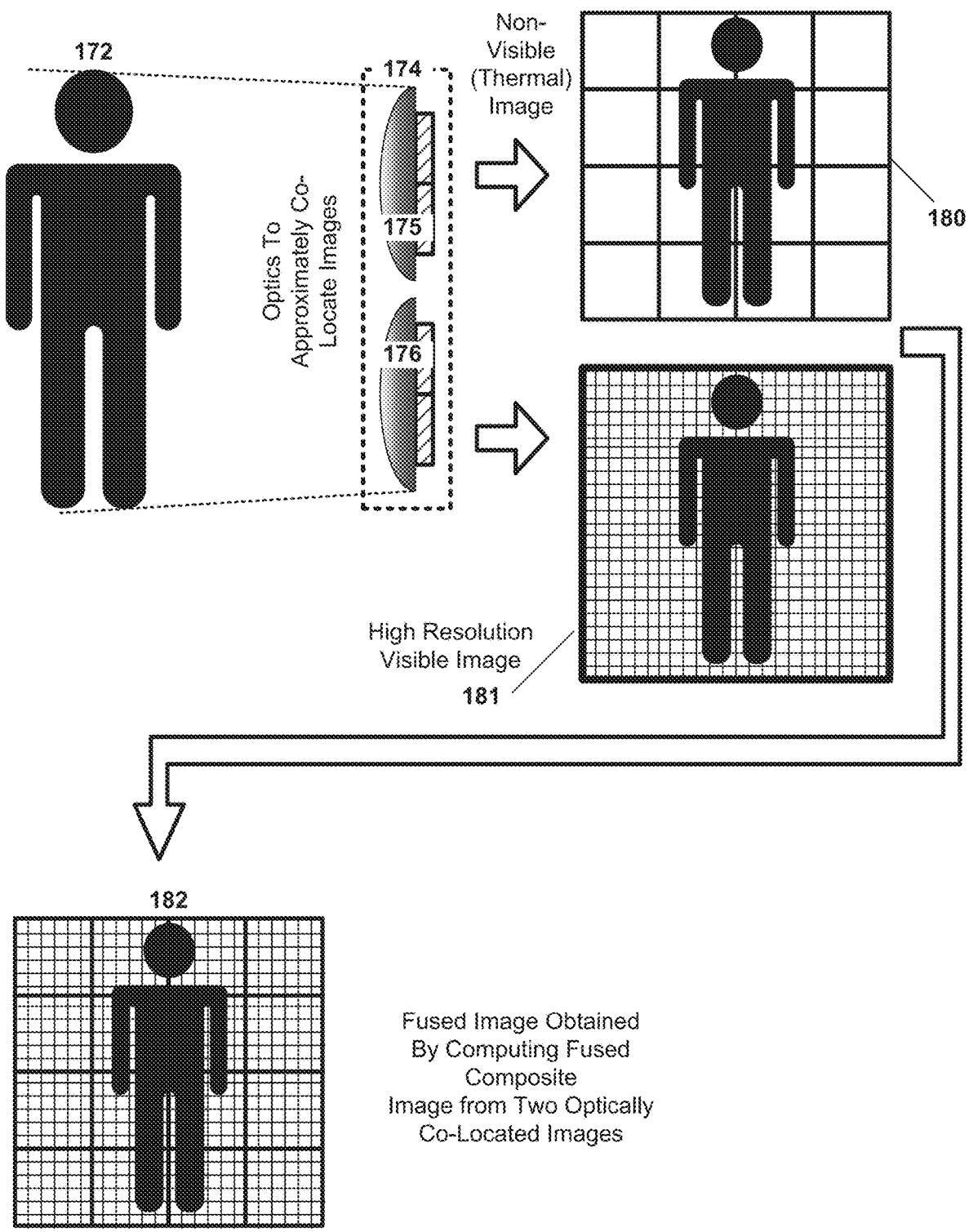
FIG. 5A shows an illustrative human subject image that is generated based on a visible light image and a non-visible radiation image collected by using visible optics and thermal imaging optics to capture approximately co-located images to create a fused image.

In one embodiment, the fusion system 48 can combine elements of visible light image and radiation image in such a manner that the subject image is readily recognizable due to visible light image, but includes emphasized features based on the radiation image. For example, FIG. 5A shows an illustrative subject image 182 for a subject 172 that the fusion system 48 can generate by fusing visible light image 181 and enhanced non-visible image 180. In an embodiment, a majority of the fused subject image 182 is based on the visible light image 181, while portions of enhanced image 180 are included to make several features stand out. It should be noted that FIG. 5A describes a method where two images 180, 181 are obtained by using an imaging component 174 including approximately co-located visible imaging optics 176 and thermal imaging optics 175 which are optically aligned by positioning in close proximity.

Figure 5B:
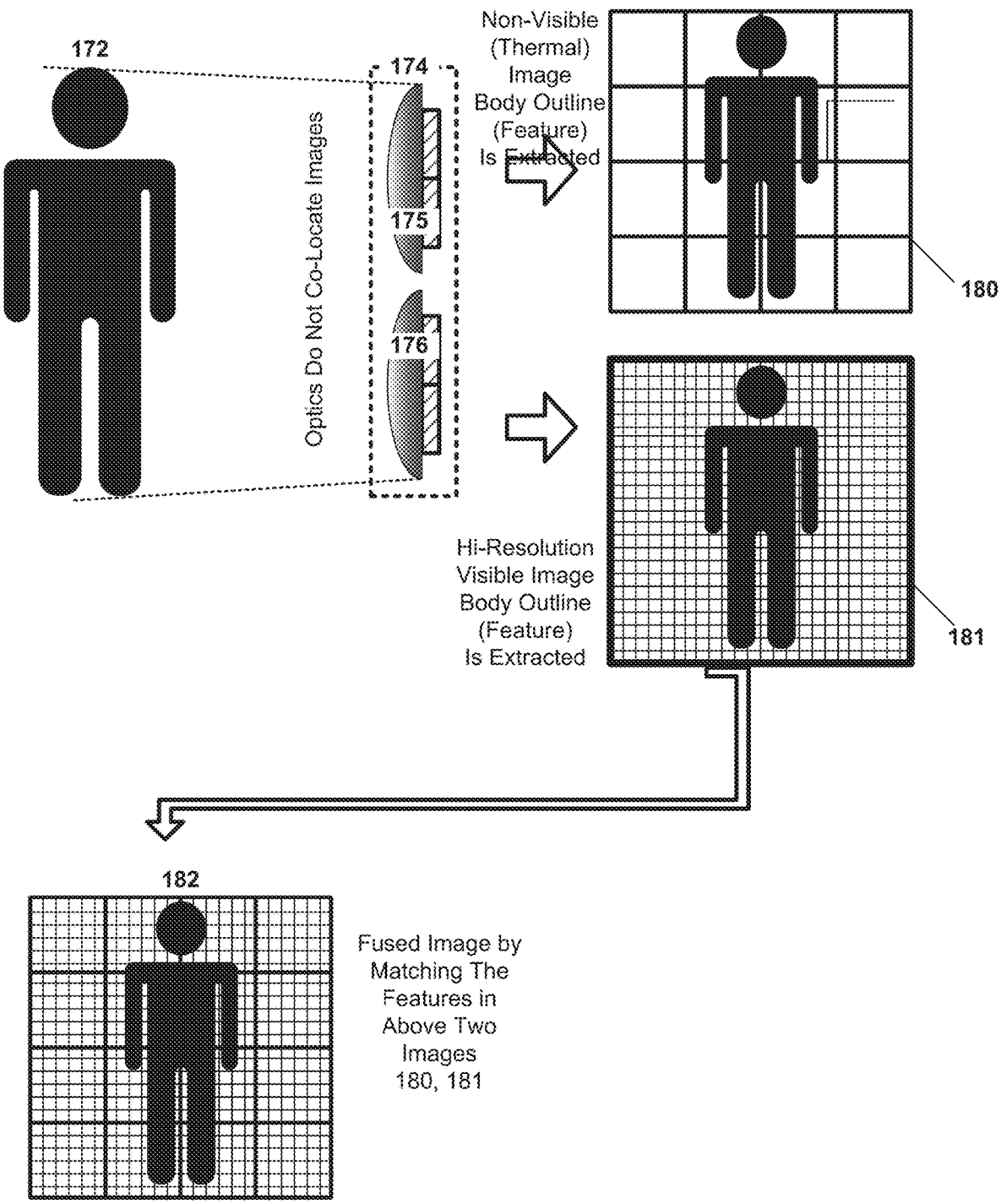
FIG. 5B shows an illustrative human subject image that is generated based on a visible light image and a non-visible radiation image which are fused by matching features in two respective images to create a fused image.
Figure 5C:
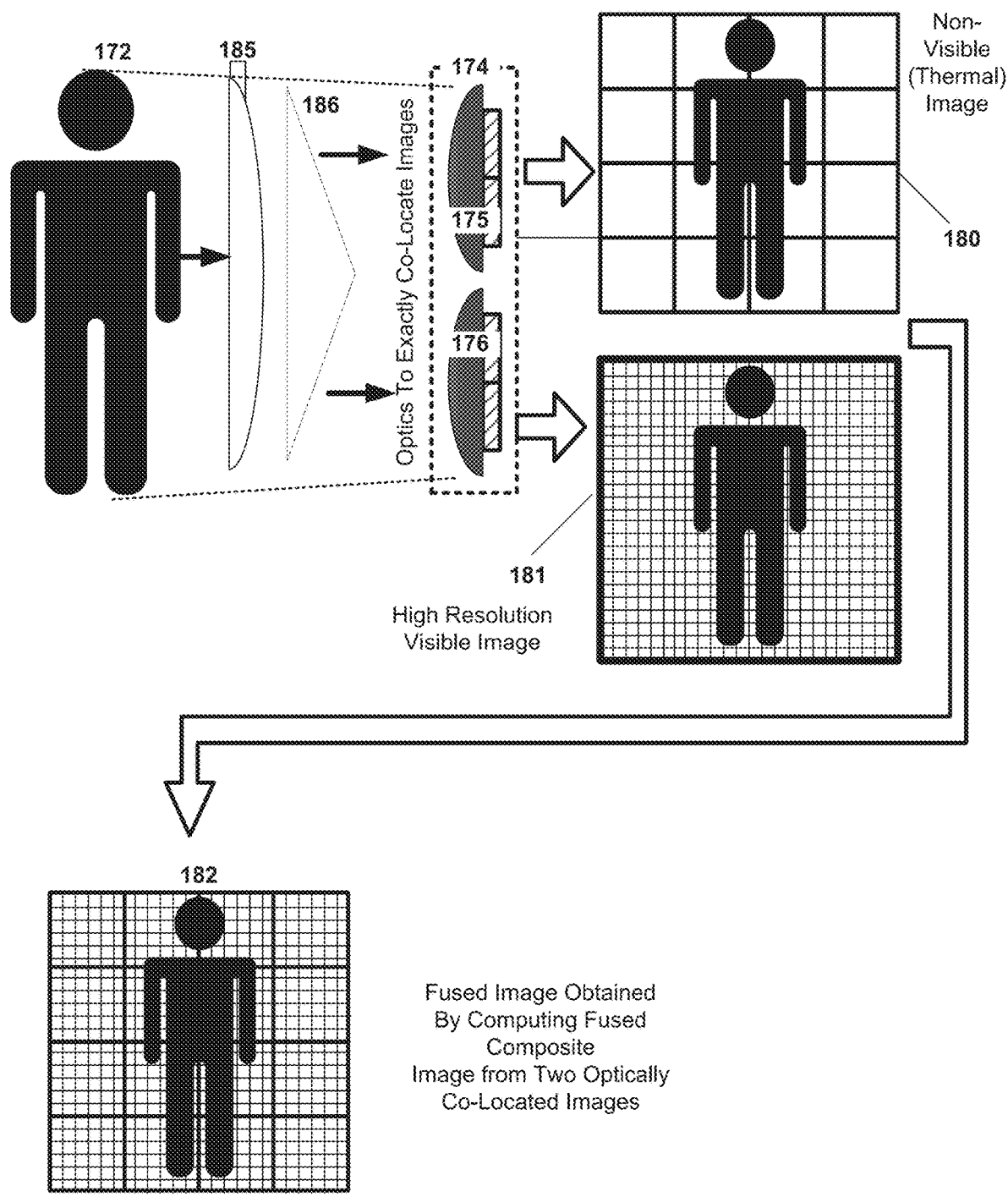
FIG. 5C shows an illustrative human subject image that is generated based on a visible light image and a non-visible radiation image collected by using visible optics and thermal imaging optics to capture exactly co-located images by using multi-spectral beam splitter and multi-spectral focusing optics to create a fused image.

Turning now to FIG. 5C, in an embodiment, a multi-spectral focusing optics 185 and multi-spectral prism 186 can be used to split object image to shine visible image through visible imaging optics 176 and thermal image through thermal imaging optics 175 to create co-located images to be used for fusion. In another embodiment, as shown in FIG. 5B, the imaging component 174 includes visible imaging optics 176 and thermal imaging optics 175 that do not co-locate the images. In this case, visible light image 181 and thermal image 180 are image processed to obtain key features in the two images, e.g. human body outline. These features are then used to align visible light image 181 and thermal image 180 to create a composite image 182.

Figure 6A:
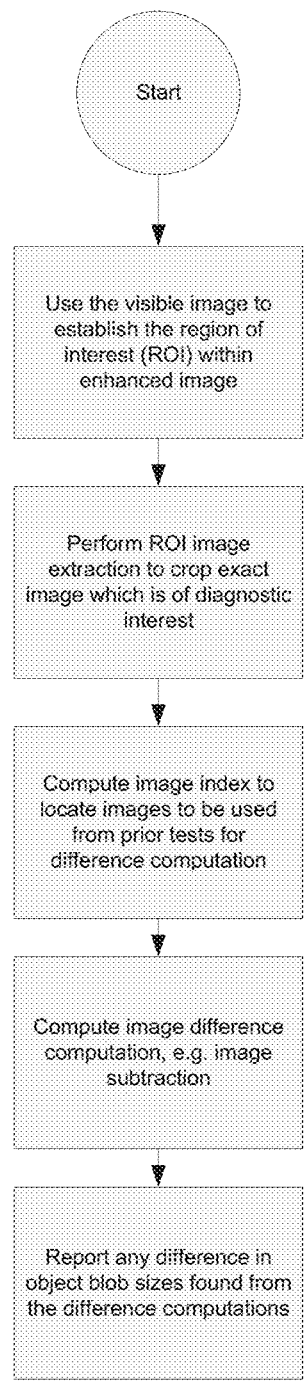
FIG. 6A-B shows illustrative method steps for automatically extracting diagnostic examination related information from a subject image according to one embodiment of the invention.
Figure 6B:
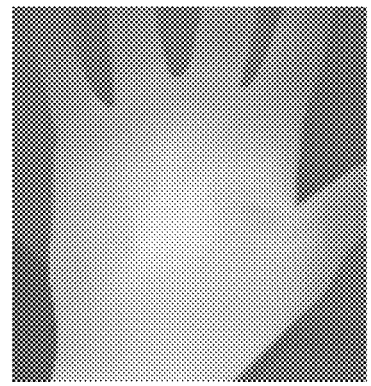

In an embodiment, diagnostic information can be automatically created for a provider. Turning now to FIG. 6A, an illustrative process for automatically creating diagnostic information according to an embodiment is shown. For example, the first step is to use the higher definition visible image and create a template or outline to help automatic cropping of the region of interest (ROI) from a larger thermal image. Once, the ROI is cropped, the system uses the database where multiple prior non-visible images are stored to perform the image differencing on the image stream. The prior non-visible images correspond to images acquired over time of the same ROI. Based on the non-visible image differences, any regions or blobs which have grown, are located back automatically. So, in a typical case, one would process a ROI containing a tumor for example. As the tumor grows, the process described in FIG. 6A will automatically detect the tumor growth.

Turning back to FIG. 1, the radiation capture system 30 could comprise a plurality of imaging systems having fields of view that can be combined to generate a larger, contiguous field of view. In this case, each imaging system can concurrently generate an image, and the images can be combined to obtain a higher resolution image of the larger field of view. Using this approach, the use of smaller, less expensive, low resolution imaging arrays is possible rather than a single higher resolution imaging array.

It should be appreciated that the teachings of the present invention could be offered as a business method on a subscription or fee basis. For example, some or all of imaging system 40 (FIG. 1), examination system 50 (FIG. 1), and/or computing device 14 (FIG. 1) could be created, maintained and/or deployed by a service provider that offers the functions described herein for customers. That is, a service provider could offer to image a subject and/or perform an examination as described above. It is understood that the present invention can be realized in hardware, software, a propagated signal, or any combination thereof. Any kind of computer/server system(s)—or other apparatus adapted for carrying out the methods described herein—is suited. A typical combination of hardware and software could be a general purpose computer system with a computer program that, when loaded and executed, carries out the respective methods described herein. Further, a specific use computer, containing specialized hardware for carrying out one or more of the functional tasks of the invention, could be utilized.

The present invention also can be embedded in a computer program product or a propagated signal, which comprises all the respective features enabling the implementation of the methods described herein, and which—when loaded in a computer system—is able to carry out these methods. Computer program, propagated signal, software program, program, program product or software, in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A non-visible mammal radiation imaging system comprising:
   means for determining that a subject is ready for medical imaging, wherein the determining is based on a temperature of the subject and a set of properties regarding a skin of the subject;
   means for obtaining a radiation image of the subject based on non-visible radiation of the subject, wherein the radiation image is obtained in response to a determination that the subject is ready for medical imaging;
   means for generating an enhanced image based on the radiation image, wherein the enhanced image has higher image quality than the radiation image and is suitable for use in a medical diagnostic examination; and
   means for displaying at least one of the radiation image or the enhanced image.

2. The system of claim 1, further comprising means for obtaining at least one characteristic of the subject, wherein the means for generating the enhanced image further uses the at least one characteristic of the subject.

3. The system of claim 1, further comprising means for obtaining a visible light image of the subject concurrently with the radiation image.

4. The system of claim 3, wherein the means for generating the enhanced image further uses the visible light image.

5. The system of claim 3, further comprising means for generating a fused image by fusing the visible light image and at least one of the radiation image or the enhanced image.

6. The system of claim 1, further comprising means for determining a set of ambient attributes for an imaging area, and means for resetting at least one of the set of ambient attributes prior to determining that the subject is ready for imaging.

7. The system of claim 1, wherein the means for determining that the subject is ready for medical imaging is configured to wait for a time period sufficient for the subject to acclimate to a temperature of an imaging area prior to performing the determining.

8. The system of claim 1, wherein the set of properties regarding the skin of the subject includes at least one of: a skin surface emissivity or a skin perspiration.

9. A handheld imaging system comprising:
   means for determining that a subject is ready for medical imaging, wherein the determining is based on a temperature of the subject and a set of properties regarding a skin of the subject;
   means for obtaining an infrared light image of the subject, wherein the infrared light image is obtained in response to a determination that the subject is ready for medical imaging;
   means for obtaining a visible light image of the subject concurrently with the infrared light image;
   means for displaying an enhanced image based on the infrared light image and the visible light image, wherein the enhanced image is suitable for use in a medical diagnostic examination; and
   means for managing at least one of the infrared light image, the visible light image or the enhanced image.

10. The system of claim 9, further comprising means for generating the enhanced image by fusing the infrared light image and the visible light image.

11. The system of claim 9, further comprising means for determining a set of ambient attributes for an imaging area, and means for resetting at least one of the set of ambient attributes prior to determining that the subject is ready for imaging.

12. The system of claim 9, wherein the means for determining that the subject is ready for medical imaging is configured to wait for a time period sufficient for the subject to acclimate to a temperature of an imaging area prior to performing the determining.

13. The system of claim 9, wherein the set of properties regarding the skin of the subject includes at least one of: a skin surface emissivity or a skin perspiration.

14. The system of claim 9, further comprising means for generating temperature data for the subject based on the infrared light image.

15. A method of inspecting a subject, the method comprising:
   determining that the subject is ready for medical imaging, wherein the determining is based on a temperature of the subject and a set of properties regarding a skin of the subject;
   obtaining a radiation image of the subject based on non-visible radiation of the subject, wherein the radiation image is obtained in response to a determination that the subject is ready for medical imaging;
   obtaining a visible light image of the subject concurrently with the radiation image; and
   generating an enhanced image based on the radiation image and the visible light image, wherein the enhanced image is suitable for use in a medical diagnostic examination.

16. The method of claim 15, further comprising:
   displaying the enhanced image to a user; and
   receiving diagnostic data from the user.

17. The method of claim 15, further comprising generating diagnostic data for the subject based on at least one of the radiation image or the enhanced image.

18. The method of claim 15, further comprising:
   determining a set of ambient attributes for an imaging area; and
   resetting at least one of the set of ambient attributes prior to determining that the subject is ready for imaging.

19. The system of claim 15, wherein the determining that the subject is ready for imaging includes waiting for a time period sufficient for the subject to acclimate to a temperature of an imaging area.

20. The system of claim 15, wherein the set of properties regarding the skin of the subject includes at least one of: a skin surface emissivity or a skin perspiration.

\* \* \* \* \*